United States Patent [19]

Monchalin

[11] Patent Number: 4,659,224
[45] Date of Patent: Apr. 21, 1987

[54] OPTICAL INTERFEROMETRIC RECEPTION OF ULTRASONIC ENERGY

[75] Inventor: Jean-Pierre Monchalin, Montreal, Canada

[73] Assignee: Canadian Patents and Development Limited, Ottawa, Canada

[21] Appl. No.: 794,777

[22] Filed: Nov. 4, 1985

[30] Foreign Application Priority Data

Nov. 28, 1984 [CA] Canada ................................ 468883

[51] Int. Cl.$^4$ ............................................. G01B 9/02
[52] U.S. Cl. ...................................... 356/352; 73/657; 356/358
[58] Field of Search .................. 356/352, 358; 73/655, 73/657

[56] References Cited

U.S. PATENT DOCUMENTS

4,129,041  12/1978  Bickel ................................. 73/657
4,379,633   4/1983  Bickel et al. ................... 356/360 X

OTHER PUBLICATIONS

Jackson et al., "Measurement of Supersonic Velocity and Turbulence by Laser Anemometry", *J. Phys. E*, vol. 4, No. 3, pp. 173–177, 3/71.

Jackson et al., "Supersonic Velocity and Turbulence Measurements using a Fabry–Perot Interferometer", *AGARD Conference Proceedings No. 193 on Applications of Non-Intrusive Instrumentation in Fluid Flow Research*, Saint-Louis, France, 5/76, pp. 6-1 to 6-13.

*Primary Examiner*—Davis L. Willis
*Assistant Examiner*—Matthew W. Koren
*Attorney, Agent, or Firm*—Yoshiharu Toyooka

[57] ABSTRACT

Non-contact reception of ultrasonic waves is accomplished by the use of a laser beam and an interferometer of the confocal Fabry-Perot type. The interferometer detects the frequency shift caused by the Doppler effect in an incident layer beam as a result of ultrasonic deformations of a workpiece. Improved stabilization and calibration techniques are disclosed.

20 Claims, 12 Drawing Figures

OPTICAL INTERFEROMETRIC RECEPTION OF ULTRASONIC ENERGY

FIELD OF INVENTION

The present invention relates to a non-contact optical technique for measuring small deformations at a surface portion of a material produced by an ultrasonic wave energy. More particularly, it is concerned with an apparatus and a method of measuring the optical Doppler shift produced in a beam of coherent light from a laser when the beam is scattered by the surface portion of the material which is undergoing deformation responsive to the ultrasonic wave energy.

BACKGROUND OF THE INVENTION

Ultrasonic non-destructive testing is one of the most important technologies to test materials and is able to detect flaws at the surface as well as inside of a material.

The surface deformations to be sensed occur in the range of frequencies extending from 0.5 MHz to 50 MHz at most. High ultrasonic frequencies are generally strongly attenuated by commonly used materials so that the range generally does not extend beyond 10 or 15 MHz. The displacements are generally much less than an optical visible wavelength (about 5000 Å) and range from a fraction of 1 Å to a few hundred Å at most. If the surface is given a velocity $v(t)(=d\delta(t)/dt$, where $\delta(t)$ is displacement), the Doppler shift is $\Delta f(t)=2v(t)/\lambda$, where $\lambda$ is the optical wavelength. Taking a peak displacement amplitude $U=20$ Å at a frequency of $f_u=2.5$ MHz ($\delta(t)=U \cos 2\pi f_u t$) gives a peak velocity $2\pi f_u U$ of about 0.03 m/s and a peak Doppler shift of about 120 KHz (2 parts in $10^{10}$ of the optical frequency). This order of magnitude shows that the velocities and relative Doppler shift are small and a very sensitive discriminator is needed to measure the surface deformations.

There have been, in the past, many interferometric systems which detect Doppler shifted radiation by ultrasonic waves and other moving targets. U.S. Pat. No. 3,355,934 issued on Dec. 5, 1967, (Foster), describes a non-contact vibration measurement system which uses a laser beam and a light frequency discriminator. The patent, however, fails to teach any specifics of the light frequency discriminator. Only description on the light frequency discriminator is found at column 5, line 13, et seq. of the patent, "Detector-discriminator can be used to put out a signal as the detected light frequency varies (similar to a standard FM discriminator) and thus measure velocity of motion of the device under study . . . ".

Michelson interferometers also have been widely used in the past for detecting Doppler shifted radiation. U.S. Pat. No. 4,046,477, Sept. 6, 1977, (Kaule), teaches an instrument of this type. This instrument, and other similar systems, detect and analyze the scattered beam from a material by using a Michelson optical interferometer. However, they have a very small light gathering efficiency when the surface being observed is not mirror-like. The reason for this is that a long optical path difference is needed for a Michelson interferometer to have adequate frequency discriminatory sensitivity and thus the central fringes of the interference are viewed under a very small angle.

The Fabry-Perot type interferometers have been studied in Review of Scientific Instruments, Vol. 39, No. 8, pp 1100–1103, August 1968, "Free surface velocity measurement of an impacted projectile by optical Doppler shift", by P. M. Johnson et al, and in Journal of Physics E: Scientific Instruments, Vol. 4, pp 170–172, 1977, "Rapid velocity sensor using a static confocal Fabry-Perot and a single frequency argon laser", by D. M. Paul et al.

U.S. Pat. No. 4,129,041, Dec. 12, 1978 (Bickel), makes mention of a Fabry-Perot interferometer to detect the Doppler shift. This patent describes mainly the use of the light absorption phenomenon to produce a filter giving the light frequency discriminator feature over a very wide acceptance angle. This property is valid for systems based on absorption by a gas, a liquid or a solid medium, since the filtering effect depends only upon the path travelled by light in the medium. The Fabry-Perot interferometer is assimilated wrongly to such filters. The acceptance angle of a Fabry-Perot interferometer is much more limited, especially in the case of the planar type which is considered in this patent. As a matter of fact, the planar Fabry-Perot has the same acceptance angle and the same étendue as the Michelson interferometer of U.S. Pat. No. 4,046,477 referred to above.

The light gathering efficiency is called "étendue" of a discriminating system and is equal to the area of its entrance aperture multiplied by the solid angle of the cone of the limit rays.

A Fabry-Perot interferometer of the confocal type (which is made of two concave mirrors having a common focal point) has a much larger étendue than the planar type.

OBJECTS OF THE INVENTION

It is therefore a principle object of the invention to provide a new and improved sensing method and apparatus useful for ultrasonic non-destructive testing of workpieces.

It is another object of the invention to provide a new and improved optical interferometric method and apparatus for sensing, without physical contact, the surface deformation of a workpiece subjected to ultrasonic energy.

It is still another object of the invention to use an optical interferometer of the confocal Fabry-Perot type with a large étendue giving a greater sensitivity of detection.

It is a further object of the invention to provide a method and mechanism for calibration of the optical interferometric apparatus in real time.

It is still a further object of the invention to provide a method and mechanism for automatically stabilizing the frequency of a laser beam at a predetermined frequency with respect to the response curve of the interferometer.

BRIEF DESCRIPTION OF THE PRESENT INVENTION

According to the present invention, the method of measuring the optical Doppler shift produced in a beam of coherent light when the beam is scattered by a surface of a material which is undergoing deformation by an ultrasonic energy. The method includes steps of transmitting an incident beam of coherent light by means of a laser system and modulating the said incident beam with a predetermined frequency fM. The modulated incident beam is directed toward the surface of the material to produce a scattered beam therefrom. The method further includes steps of transmitting the scattered beam through an interferometer of the confocal Fabry-Perot interferometer type which exhibits a frequency response curve including a peak therein, for producing an optical interferometer signal. The optical signal is detected to generate an electrical signal responsive thereto which is then processed to generate an output indicative of the Doppler shift in the scattered beam. The present method includes an additional step of filtering the electrical signal through a bandpass filter tuned at the predetermined frequency of $f_M$ to produce a calibration signal.

The apparatus of the present invention is for measuring the Doppler shift produced in a beam of coherent light when the said beam is scattered by a surface portion of a material undergoing deformation responsive to the presence of an ultrasonic wave. The apparatus comprises a laser system for transmitting an incident beam of coherent light and modulation means for modulating the incident beam with a predetermined frequency $f_M$. The apparatus further comprises optical assembly means for directing the modulated incident beam toward the surface portion of the material to produce a scattered beam therefrom and for transmitting the scattered beam. An interferometer of the confocal FabryPerot type is disposed in the path of the scattered beam transmitted by the optical assembly means for producing an optical interferometer signal. The interferometer exhibits a frequency response curve having a peak. The apparatus further includes photodetecting means for detecting the optical interferometer signal to generate an electrical signal responsive thereto which optical circuit means process to produce an output indicative of the Doppler shift in the scattered beam. The apparatus is provided additionally with calibration circuit means having a bandpass filter tuned at the said predetermined frequency $f_M$, which calibration circuit means are connected to the output circuit to produce a calibration signal with which the said output indicative of the Doppler shift can be calibrated.

BRIEF DESCRIPTION OF THE DRAWINGS

For a more complete understanding of the present invention and for further objects and advantages thereof, references may now be made to the following description taken in conjunction with the accompanying drawings in which.

DETAILED DESCRIPTION OF THE PREFERRED EMBODIMENTS

Figure 1:
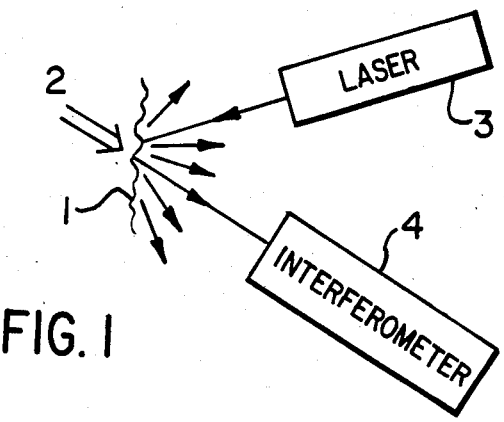
FIG. 1 shows a basic arrangement of instruments to demonstrate the principle of the present invention.
Figure 2:
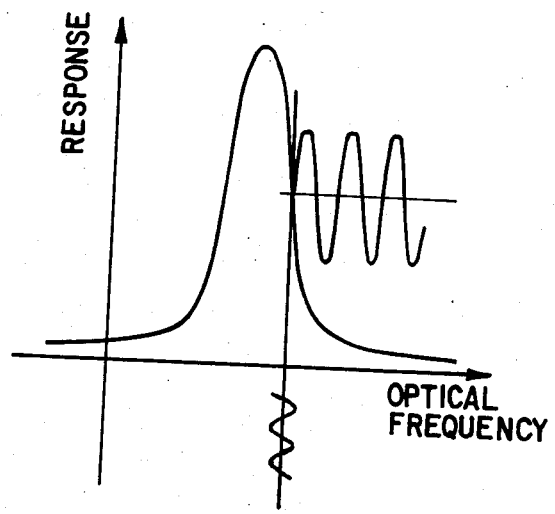
FIG. 2 is a frequency response curve of an optical interferometer used in the present invention, FIGS. 3a and 3b indicate sidebands created by frequency modulation of an incident laser beam.

Turning now to the drawings, FIGS. 1 and 2 explain the basics of the technique considered in this application.

As seen in FIG. 1, a surface portion 1 of a workpiece is undergoing deformation by an ultrasonic energy 2. A laser beam from a source 3 is scattered by the surface portion and as it is scattered, it is frequency modulated as a result of the Doppler effect. The scattered beam is analyzed by an optical frequency spectrum analyzer (interferometer) 4 to measure the Doppler shift which is related to the surface deformation of the workpiece.

Figure 3A:
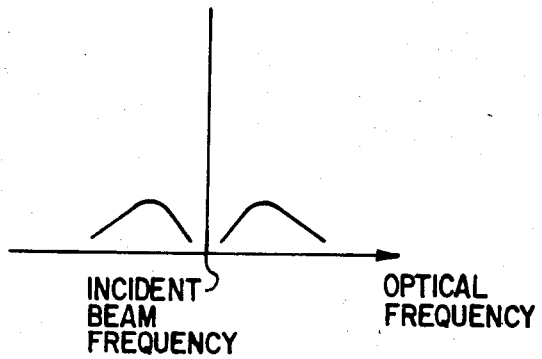
Figure 3B:
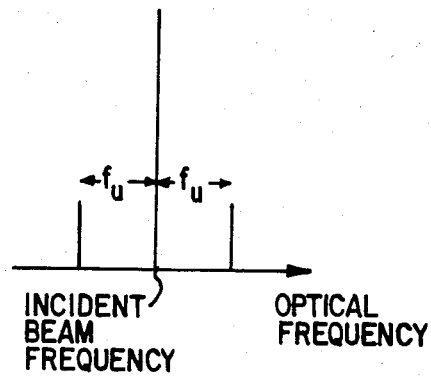

FIG. 2 shows that the frequency 5 of the optical source and the response curve 6 of the interferometer, should be properly set with respect to one another and that a control means between the two should be devised. As seen in FIG. 2, the frequency of the optical source is located near the half maximum of the peak or near the point where the second derivative of the curve is zero. This analysis is, however, strictly valid when the frequency of the ultrasonic waves is much less than the width of the interferometer. In fact, the ultrasonic displacement produces two weak sidebands on both sides of the optical frequency of the incident light beam. This is shown in FIG. 3a for pulse ultrasonic excitation and in FIG. 3b for continuous excitation ($\delta(t) = U \cos 2\pi f_u t$, in this case the ratio of the sidebands to the central peak is $2\pi U/\lambda$). In consequence, the interferometer which gives the maximum response for a given ultrasonic frequency $f_u$ has a bandwidth of the order of $f_u$. For a given interferometer bandwidth, the response increases linearly with frequency at low frequencies since the Doppler shift is proportional to the frequency, levels off at a frequency of the order of the bandwidth and then decreases at higher frequencies. When the workpiece is in motion, an additional Doppler shift of frequency may occur. When the motion is perpendicular to the line of sight of the discriminating system, this effect is negligible, but it may be troublesome when the motion is along the line of sight. For instance, a normal velocity of 1 m/s gives for $\lambda = 1$ μm a shift of 2 MHz. In this case, an interferometer with a sufficiently broad bandwidth should be used (but with a reduced sensitivity) or the frequency variation should be compensated by a tracking means. Another important factor to be accounted is the roughness of the surface which scatters the incident beam in various directions, so in practice it will be very important to devise a discriminator which can accept rays within a sufficiently broad angular aperture and, therefore, has a large "étendue".

Figure 4:
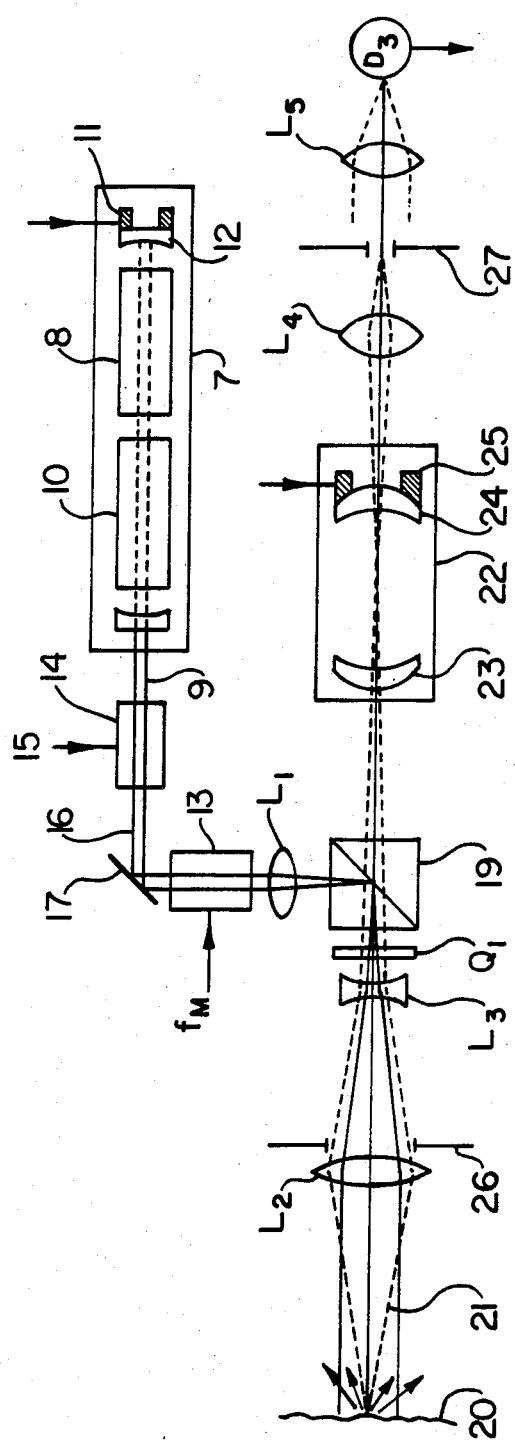
FIG. 4 is a schematic drawing of an embodiment according to the present invention.

Referring now to FIG. 4, one embodiment of the present invention is shown in which, a laser system 7 includes a laser 8 emitting an incident beam 9 of substantially monochromatic coherent light. The laser system 7 further has a first electro-optic cell (an intracavity phase shifter) 10 and a piezoelectric pusher 11 holding a mirror 12, forming a part of the lasing cavity. The first electro-optic cell 10 and a piezoelectric pusher 11 change the oscillating conditions of the laser system to vary the frequency of the coherent light. A second electro-optic cell 13 is positioned in the path of the incident beam 9 to phase modulate the beam. The second electro-optic cell 13 is made of an electro-optic crystal placed between two electrodes and is driven by a sine wave voltage at frequency $f_M$. It produces a phase modulation which is used for signal calibration.

In some instances, the laser system 7 may be followed by an amplification laser sub-system 14. This laser amplification sub-system 14 provides a single frequency light signal of the same frequency as the oscillator, but at a much higher power, which increases the sensitivity of the whole apparatus. In most applications, the ultrasonic displacements are transitory, so that amplification sub-system 14 is operated only for a time interval sufficient to capture them by means of a trigger signal 15. This sub-system 14 may be made of one, or of a series of, laser amplifiers or of a laser oscillator locked to single mode operation by injection from the laser oscillator. For example, the oscillator may be a stable Nd-YAG CW single TEMoo mode laser and the amplifiers or the injection locked laser made by Nd-YAG rods pumped by flashlamps. Duration of emission of flashlamps are typically between 100 $\mu$s to 1 ms, which provides a viewing time window sufficient for most applications.

The phase modulated incident beam 16 passed through an optical assembly means. In this embodiment, the optical assembly means are made up of such optical elements as lenses $L_1$, $L_2$ and $L_3$, a mirror 17, a quarter-wave plate $Q_1$ and a polarizing beam splitter 19. The optical assembly means project the phase modulated incident beam 16 onto a surface portion 20 of a workpiece which is undergoing deformation in the influence of an ultrasonic wave. The phase modulated incident beam is scattered from the surface portion of a workpiece but due to the Doppler effect caused by the vibration of the surface portion, the scattered beam is additionally frequency modulated. This scattered bean 21 from the workpiece is received by lenses $L_2$ and $L_3$, quarterwave plate $Q_1$, and polarizing beam splitter 19. The combination of lenses $L_2$ and $L_3$ is such that a confocal Fabry-Perot interferometer 22 is used properly as will be explained below. Once lenses $L_2$ and $L_3$ have been set, lens $L_1$ can be determined to produce on the workpiece an illuminated region of appropriate size. For several industrial applications, it would be convenient to take a working distance (distance between the workpiece and the optical assembly means) of about 2 m, a maximum spot size of about ½ inch and a minimum of the order of about 0.1 mm. The illuminated region is viewed along the same direction as that of illumination through the use of the polarizing beam splitter 19. A polarizing beam splitter has the property to transmit for a given wavelength nearly all the light polarized parallel to the plane of incident and to reflect nearly all the light polarized perpendicular to the plane of incidence. As seen in FIG. 4, vertically polarized incident beam is nearly completely reflected by the polarizing beam splitter 19 and then sent through the quarter-wave plate $Q_1$ oriented at 45° which transforms it into circularly polarized beam. On return from the surface portion 20, the scattered beam 21 after going through the quarter-wave plate $Q_1$ is polarized horizontally and is then nearly completely transmitted towards a confocal Fabry-Perot interferometer 22. Obviously, the illuminating path and the viewing path can be made different, but the configuration described above has the advantage to require a minimum of readjustments when the working distance is changed and, in particular, enable to probe workpieces which are in motion and have a displacement along the line of sight (this is the case of several industrial applications).

The confocal Fabry-Perot interferometer 22 is made of two concave mirrors 23 and 24 of an equal radius, one of which is mounted on a piezoelectric pusher 25 so that the spacing between the mirrors may be varied for fine tuning with respect to the laser frequency. Lenses $L_4$ and $L_5$ are used to focus the scattered beam from the confocal Fabry-Perot interferometer 22 on a photodetector $D_3$. Apertures 26 and 27 limit the inclination of the light rays to satisfy the proper operating conditions of the interferometer 22. In order to use all the light energy provided by the laser system, the illuminated spot size on the surface portion 20 should match exactly aperture 27 and the usable area of the central fringe inside the confocal Fabry-Perot interferometer 22.

The system described above uses a confocal Fabry-Perot made of two spherical mirrors in which the interference fringes are caused by aberrations of the third order. These aberrations can be corrected, for example, by having a correcting glass slab with a proper variation of thickness or a lens of suitable curvature halfway between the mirrors, giving then a central flange of larger area, a larger étendue and a more sensitive receiving system.

Figure 5:
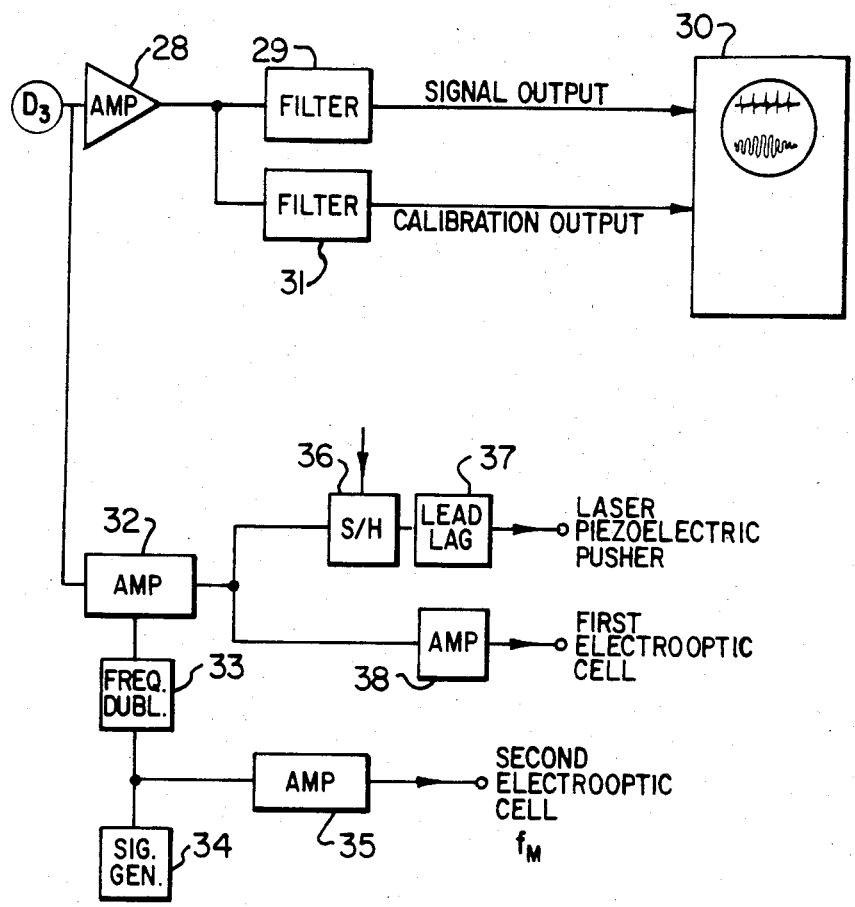
FIG. 5 is a block diagram of the embodiment shown in FIG. 4.

FIG. 5 shows an electrical block diagram of the embodiment of the present invention shown in FIG. 4. As seen in the figure, the electrical signal from the photodetector $D_3$ is amplified by an RF broadband amplifier 28 whose output is filtered by a bandblock filter 29, tuned at the frequency $f_M$ to reject a signal of that frequency. The output of the bandblock filter 29 is an indication of the Doppler shift in the scattered beam and is displayed on a two-channel oscilloscope 30. The filter 29 is used to eliminate a spurious noise signal by the sine wave voltage at the frequency $f_M$ which is applied to the second electrooptic cell 13 for phase modulation for the purpose of signal calibration.

According to the present invention, the optical instrument shown in FIG. 4 is calibrated by the use of the second electro-optic cell 13. As described previously, the second electro-optic cell 13 is made up of an electro-optic crystal sandwiched between two electrodes and is driven by a sine wave voltage at frequency $f_M$. The cell produces a phase modulation in the incident beam 9 which modulation is analogous to that produced by an ultrasonic wave at the surface portion. Consequently, this modulation can be used as a reference for calibration. Knowing the amplitude of the voltage applied to the second electro-optic cell 13, and the electro-optic constants of the crystal, the phase modulation produced can be determined. For example, if a crystal such as ADP or KDP is used in a transverse configuration (direction of propagation perpendicular to the optical z axis, electric field applied along the z direction, laser polarized perpendicularly to the z direction), it can be shown that a voltage $V \cos 2\pi f_M t$ corresponds to a surface displacement of the workpiece $\ln^3{}_o r_{63} V \cos(2\pi f_M t)/4e$, where $l$ is the length of the crystal, $n_o$ is its ordinary index, $r_{63}$ is one of its electro-optic constants and $e$ is the electrode spacing. In practice, a frequency $f_M$ lower (such as 0.5 MHz) or higher (such as 20 MHz) than the frequency band of the signal is used so it can be easily separated from the signal by a filter. Other phase modulators may be used as well, such as an undamped piezoelectric crystal which is excited continuously at a compression mode and is provided with a reflecting coating on one side to reflect the light from the laser before directing it to the workpiece.

In the embodiment shown in FIG. 5, a crystal bandpass filter 31, tuned at $f_M$, produces a calibration output which is displayed on the two channel oscilloscope 30 simultaneously with the Doppler shifted signal output from the filter 29. Simultaneous observation of the two outputs permits calibration, or the outputs can also be recorded. Of course, the calibration output from the filter 31 can be further rectified and used to provide real time calibration of the Doppler shifted signal output electronically.

Another feature of the present invention is the technique used to lock the laser frequency to the most sensitive operation point of the Fabry-Perot resonance curve, i.e. approximately at half maximum of the peak or a point where the second derivative of the curve is zero. The laser frequency fluctuations occur mostly below 1 MHz. At low frequencies, they are caused by the thermal expansion of the laser cavity spacing or of its intra-cavity elements. In the audio range and above, they are caused by vibrations. Up to the upper limit of the audio range (about 20 KHz), compensation is obtained by varying the cavity length with a piezoelectric pusher 11 which supports one of the mirrors 12 and is driven by the error voltage derived from the stabilization loop described below. At higher frequencies, compensation is obtained by an intra-cavity rapid phase shifter 10 which is an electro-optic cell identical to the one described above for real time calibration. This invention has the distinguishing feature that frequency compensation is obtained independently of laser amplitude variations.

The stabilization mode shown in FIGS. 4 and 5 is particularly useful for a workpiece which is in sufficiently rapid motion along the line of sight to shift the frequency by an amount of the order of the Fabry-Perot bandwidth or more. The stabilization scheme is based on the fact that the best stabilization point on the Fabry-Perot response curve is at a zero of the second derivative of this curve. This zero is automatically tracked by phase detecting the second harmonic of the frequency modulation at $f_M$: this stabilization point corresponds to a null of the second harmonic. As seen in FIG. 5, the signal from photodetector $D_3$ is sent to the input of a high frequency lock-in amplifier (phase detector) 32 referenced by a signal at $2f_M$ from a frequency doubler 33 doubling the frequency of the output derived from the signal generator 34 which drives the phase modulator (the second electro-optic cell 13) through a high voltage amplifier 35. The output of the lock-in amplifier 32 is then applied to the piezoelectric pusher 11 of the laser system 7 through a sample and hold circuit 36 and a lead-lag circuit 37, and the intra-cavity phase shifter (the first electro-optic cell 10) through a wide band high voltage amplifier 38. The sample and hold circuit 36 holds the output of the lock-in amplifier 32 applied to the piezoelectric pusher 11 until the amplification laser sub-system 14 fires again. This mode of frequency locking is independent of the laser or signal amplitude.

Figure 6:
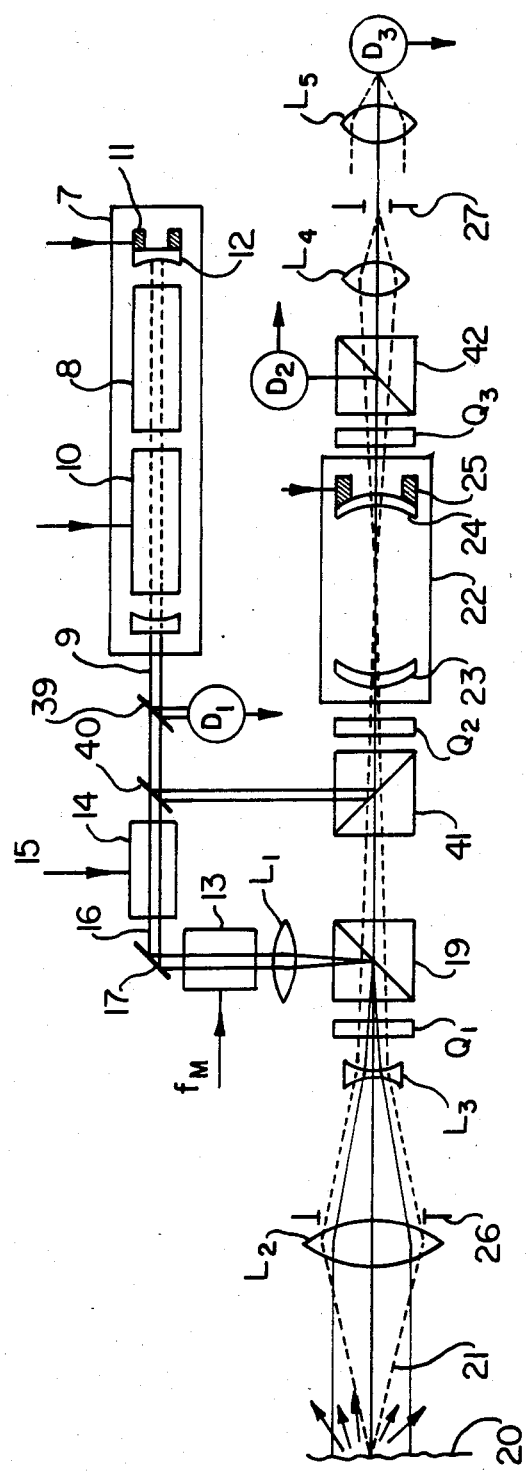
FIG. 6 is a schematic drawing of another embodiment according to the present invention.
Figure 7:
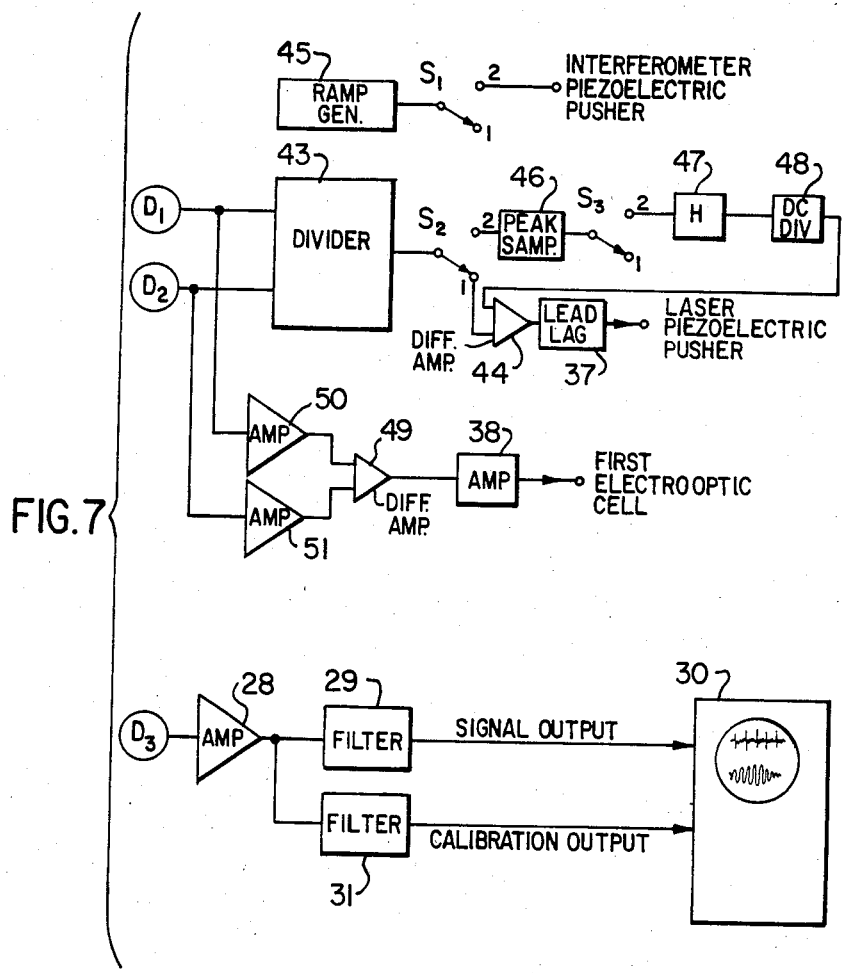
FIG. 7 is a block diagram of the embodiment shown in FIG. 6.

FIGS. 6 and 7 show another embodiment of the present invention. In these figures, like numerals are used to designate like parts of the embodiment shown in FIGS. 4 and 5.

In this embodiment, the stabilization (locking-in of the laser frequency) is carried out at the most sensitive operation point of the Fabry-Perot resonance curve, that is to say, approximately at the half maximum of the peak.

As seen in FIG. 6, two beam splitters 39 and 40 are located at the output of the laser system 7 and pick up a small fraction of its intensity. The beam splitter 39 sends a beam to a photodetector $D_1$ which is used to monitor the laser amplitude fluctuations. The beam splitter 40 and a polarizing beam splitter 41 send a beam through the quarter-wave plate $Q_2$ into the Fabry-Perot interferometer 22, which is colinear with the scattered beam 21 coming from the surface portion 20 of the workpiece. A polarizing beam splitter 42 reflects the beam picked up by the beam splitter 40 onto a photodetector $D_2$, which is used to monitor the laser frequency fluctuations. As in the arrangement shown in FIG. 4, the incident beam from the laser system 7 is vertically polarized and the scattered beam reflected from the surface portion is horizontally polarized by the quarter-wave plate $Q_1$ oriented at 45° to the vertical located after the aperture 26. Quaterwave plate $Q_2$ is oriented at 45° to the vertical. It produces circularly polarized ligh and is used to eliminate feedback from the interferometer into the laser. Quaterwave plate $Q_3$ is antiparallel to $Q_2$ and restore the polarization of the beams to those in front of $Q_2$. This arrangements ensures that the polarizing beam splitters 41 and 42 transmit nearly all the intensity coming from the surface portion and reflect nearly all the intensity of the beam directly issued from the laser system 7 via the beam splitter 40. As in FIG. 4, in some instances, the laser system 7 may be followed by an amplification laser sub-system 14 which is triggered by a trigger signal 15.

Now turning to FIG. 7, an error signal representing the variations of laser frequency at low frequencies is obtained by dividing by an analog divider 43, the signal from $D_2$ which monitors the output of the Fabry-Perot interferometer 22 by the signal given by $D_1$, which monitors the laser amplitude variations. The error voltage which is applied to the laser piezoelectric pusher 11 through the leadlag circuit 37, providing integration and damping is obtained by comparing, at a differential amplifier 44, the error signal above with a reference signal obtained when the laser frequency is properly set at the most sensitive point of the Fabry-Perot response curve, which is about at half maximum of the peak. This reference signal is obtained when switches $S_1$, $S_2$, and $S_3$ are on position #2. In this case, a ramp generator 45 sweeps periodically the Fabry-Perot resonance and the resonance peak height is sampled by a peak sampler 46. When the switches are returned to position #1 (locking position), the peak height is held by a hold circuit 47 and then divided by two by a DC divider 48, to produce the reference signal used for stabilization. To detect variations at higher frequencies, a wide band differential amplifier 49 is used. In order that the difference represents accurately the laser frequency variations, the signals from detectors D1 and D2 should be amplified to the proper levels. Gain adjustments are performed by amplifiers 50 and 51 when the Fabry-Perot resonance is tuned so its maximum coincides with the laser frequency. In this case, the Fabry-Perot is not very sensitive to fluctuations of frequency and the output of the differential amplifier 49 should be nearly zero. This output is then applied to the wide band high voltage amplifier 38 which drives the intra-cavity electro-optic cell 10 which itself compensates rapidly for laser frequency variations.

Figure 8:
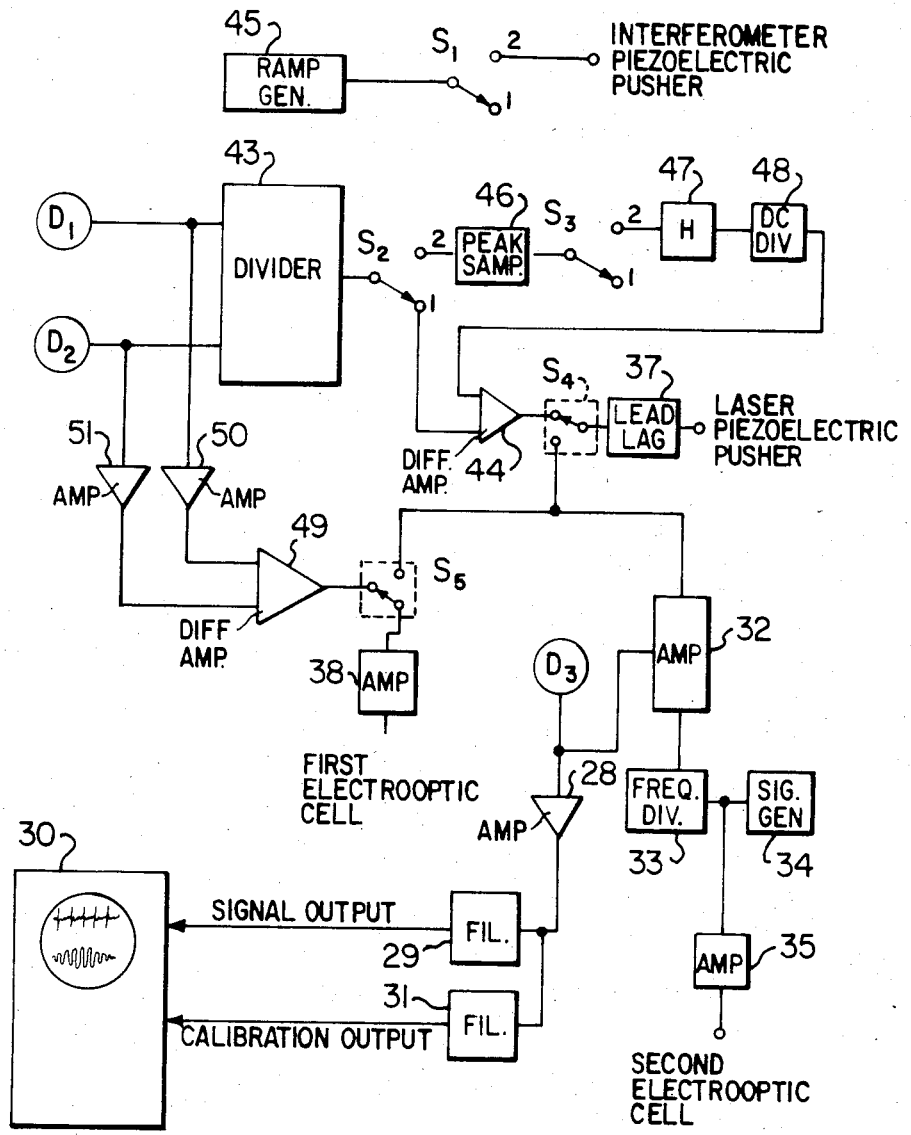
FIG. 8 is a block diagram of another embodiment.

It is, of course, possible to combine the electrical block diagrams of FIGS. 5 and 7, as shown in FIG. 8. By using proper switches, the diagram of FIG. 8 can be made operative in either of the stabilization modes. Of course, for pulsed operation, switches $S_4$ and $S_5$ must be triggered coincidently with the amplification laser sub-system 14.

Figure 9A:
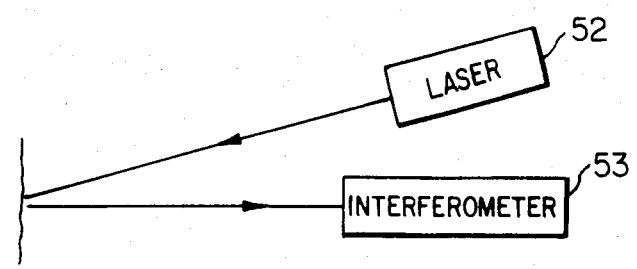
FIGS. 9a and 9b show possible implementation of the present invention for non-destructive testing.
Figure 9B:
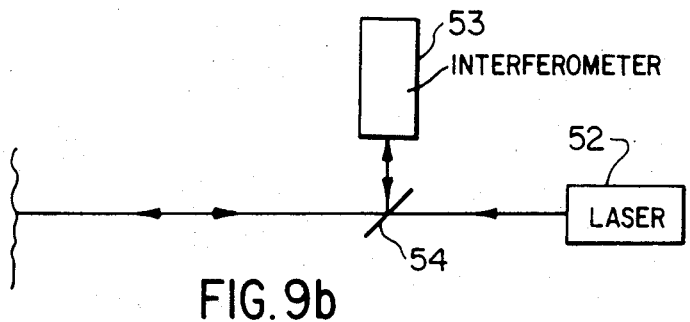

FIGS. 9a and 9b show possible implementations of the present invention for non-destructive testing where the ultrasonic deformation is generated by a high power pulse laser beam generated from a pulse laser 52. An interferometric receiving unit 53 receives the scattered beam. In the figures, the ultrasonic wave is always generated on or next to the view spot. In FIG. 9b, in particular, a dichroic beam splitter 54 permits the high power pulse beam to be sent colinearly with the incident beam from the receiving unit. In some instances, since the intense generating laser pulse may produce ablation of the surface portion, it may be found better to generate ultrasonic wave not on the view spot but next to it. In this case, the incident and scattered beam of receiving unit 53 can be steered parallel to the generating laser beam. This arrangement will also enable to probe conveniently the workpiece in motion along the line of sight.

It should also be noted that in practice, if the inspection procedure calls for a given illumination spot size on the workpiece, a lens combination $L_2$ and $L_3$ is calculated to give an image size inside the Fabry-Perot which matches the usable portion of the central fringe. If the spot size is decreased from this optimum limit size by moving $L_1$, the bandwidth is not significantly reduced and the signal does not change since the same light energy is collected (assuming uniform ultrasonic displacement over the illuminated spot). One should note that, when the illuminated spot is reduced, the collecting optical system is not optimized anymore since all the available étendue of the Fabry-Perot is not used. If some flexibility on the spot size is required, an optical viewing system more complex than $L_2$ and $L_3$ is required. This system should have a variable focal length (zoom optical system) and can be realized using a commercial zoom telephoto lens used in place of $L_2$ with or without a diverging element such as $L_3$. In the opposite case, when the illuminated region is increased, the aperture 27 being left at the same size, the signal decreases since the brilliance of the spot decreases. If the aperture 27 were opened, a further decrease will occur because several Fabry-Perot fringes will be seen by the detector.

It should be noted that the system is not limited to the detection of bulk ultrasonic waves, but also can be used to detect surface waves as well. If the surface wave is made to converge to a point, a small circular spot may be illuminated as described above. If the surface wave propagate with a linear wavefront of a predetermined width, a small line of a sufficient length is illuminated by using, for lens $L_1$, suitable cylindrical optics. This line shjould be less than a ultrasonic wavelength across. The received beam is restored to circular symetry by using cylindrical optics for lens $L_2$ or $L_3$.

Current optical technology enables to produce commercially confocal spherical Fabry-Perot interferometers with thickness ranging from a few cm to 50 cm and more for various laser wavelengths. Bandwidths ranging from several 10 MHz down to 1 MHz can be obtained. Mirrors with adequate sphericity quality can be manufactured and it is possible to adjust their spacing precisely to the confocal configuration. Fine tuning of the bandpass frequency is obtained by mounting a mirror on a piezoelectric pusher which enables to vary the mirror spacing. As an example, a confocal system 50 cm long with 90% reflectivity mirrors has a bandwidth of about 10 MHz and an étendue at 1.06 $\mu$m (wavelength of a Nd YAG laser) of about 0.2 mm sr. This is approximately the étendue given by a spot 10 mm in diameter located 2 m away from a collecting lens 10 cm in diameter and, therefore, this confocal Fabry-Perot is well adapted to remote ultrasonic wave detection. Further analysis shows that the received signal is proportional to the étendue, to the spectral resolving power (defined as the ratio of the frequency to the bandwidth) of the Fabry-Perot and to the brilliance of the illuminated spot. The product étendue x resolving power is a function only of the mirrors spacing and is independent of the mirrors reflectivity. Replacing a mirror set by another one of different reflectivity changes the spectral resolving power, but does not change the received signal, if the brilliance is kept constant (this requires adjusting the spot size or the collecting optics). However, further analysis shows that in the case of quantum noise limited detection, the signal-to-noise ratio increases with the optical resolving power. The resolving properties of the system can then be varied to optimize inspections in various circumstances: according to the material inspected, and in particular, according to its ultrasonic attenuation characteristics, and if the piece is stationary or in motion along the line of sight, a bandwidth more or less narrow will be required. Therefore, this system allows more flexibility than a two-waves interferometer such as those of U.S. Pat. No. 4,388,832 referred to above, in which the resolving power is proportional to the path length difference. In these interferometers, the resolving power is, as a matter of fact, fixed since it is impracticable to change the length of the interferometer arms (besides it may have very adverse effects on the étendue) and a high resolving power may require an arm too long to be practicle. Still further analysis of the confocal Fabry-Perot receiving system confirms what was stated previously that the maximum response for a given ultrasonic frequency $f_u$ is obtained when the bandwidth is of the order of $f_M$. It confirms also that, for a given Fabry-Perot, the response increases linearly with frequency at low frequencies, levels off at a frequency of the order of the bandwidth and then decreases at higher frequencies. For many industrial applications on workpiece stationary or in slow motion along the line of sight, it is found that a bandwidth of 10 to 20 MHz represents a good trade-off. Another advantage of the confocal FabryPerot set-up with respect to a two-wave interferometer is that, because of its relatively small size and the absence of the liquid cell necessary to increase the étendue, it can be made very stable and immune from vibrations and thermal drifts effects. Current technology which usesa rigid Super-Invar [trademark] structure in a temperature controlled enclosure limits drifts to a few MHz per hour and gives a short term stability better than 1 KHz.

It may be convenient in an industrial environment to have the Fabry-Perot and especially the laser located sufficiently far away from the inspection area. This can be done by using optical fibers or optical wave guides. A single fiber can be used to guide laser light from the output of electro-optic cell 13 to lens $L_1$. An additional polarizer or birefringent plate is to be used to compensate fiber birefringent and to provide a polarized beam at the input of $L_1$. On the receiver side, a fiber or a fiber bundle may be used after reflection by the polarizing beam splitter 17 to conduct light to a lens combination which enables proper illumination of the confocal Fabry-Perot.

It is also possible that some simplification will occur if a laser oscillator with little frequency jitter can be made. In this case, the first electro-optic cell 10 and its associated electronic circuit may be eliminated.

Figure 10:
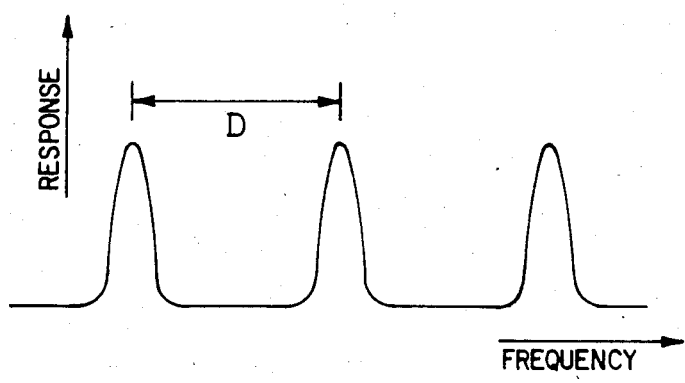
FIG. 10 is a response curve of a confocal Fabry-Perot interferometer exhibiting equidistant peaks.

The system has been described with a single frequency laser (single mode laser). However, as can be seen in FIG. 10, which shows a response curve of a confocal Fabry-Perot interferometer, it is also possible to use a multimode laser if the intermode spacing corresponds exactly to n times (n being an integer) the free spectral range D (i.e. the laser cavity length should be $\simeq 2/n$ the confocal Fabry-Perot spacing). The response curve has peaks which are equidistant with the free spectral range D between them. In practice, it is only possible to fulfill this requirement for a 3 modes (3 frequencies) laser, since modes are not exactly equidistant because of the dispersion of the laser medium, but this could be useful to relax laser requirements in some cases.

I claim:

1. A method of measuring the optical Doppler shift produced in a beam of coherent light when the said beam is scattered by a surface portion of a material undergoing deformation responsive to the presence of an ultrasonic wave, comprising steps of:
   transmitting an incident beam of coherent light by means of a laser system,
   phase modulating the said incident beam by a predetermined frequency $f_M$,
   directing the said modulated incident beam toward the surface portion of the material undergoing the deformation to produce a scattered beam therefrom,
   transmitting the scattered beam through an interferometer of the confocal Fabry-Perot type exhibiting a frequency response curve having a peak for producing an optical interferometer signal,
   detecting the said interferometer signal to generate an electrical signal responsive thereto,
   processing the said electrical signal to generate an output indicative of the Doppler shift in the scattered beam,
   filtering the electrical signal through a bandpass filter tuned at the said predetermined frequency $f_M$ to produce a calibration signal, and
   calibrating the said electrical signal by feeding back the said calibration signal so that the said output is properly calibrated in real time.

2. The method according to claim 1 wherein the step of directing the said modulated incident beam comprising further steps of:
   polarizing the said incident beams and the said scattered beam differently from each other, and
   sending the said incident beam toward the surface portion of the material in a direction substantially normal thereto and the said scattered beam toward the interferometer.

3. The method according to claim 2 further comprising steps of:
   obtaining a stabilization signal by processing the said electrical signal using a reference signal of the frequency $2f_M$, and
   applying the said stabilization signal to the laser system for adjusting the frequency of the coherent light to match the frequency corresponding to a zero of the second derivative of the said frequency response curve of the interferometer.

4. The method according to claim 3 wherein the laser system is a multi-mode laser system.

5. The method according to claim 2 further comprising steps of:
   generating an amplitude fluctuation signal,
   generating a frequency fluctuation signal,
   processing the said signals to produce a first and a second signals, and
   applying the said first and the second signals to the laser system to adjust the frequency of the coherent light so that the frequency of the incident beam is set at about half maximum of the peak of the frequency response curve of the interferometer.

6. The method according to claim 5 wherein,
   the step of generating the amplitude fluctuation signal comprises a step of receiving a first portion of the incident beam, and
   the step of generating the frequency fluctuation signal comprises steps of (a) passing a second portion of the incident beam through the interferometer colinearly with the scattered beam, and (b) collecting the said second portion of the incident beam after it has passed through the interferometer.

7. The method according to claim 6 wherein the laser system is a multi-mode laser system.

8. The method according to claim 1 further comprising the steps of:
   transmitting a high power pulsed laser beam, and
   illuminating the said surface portion of the material with the said high power pulsed laser beam substantially colinearly with the modulated incident beam by means of a dichroic beam splitter so that the ultrasonic wave is generated in the material.

9. The method according to claim 3 further comprising steps of,
   transmitting a high power pulsed laser beam, and
   illuminating the said surface portion of the material with the said high power pulsed laser beam substantially colinearly with the modulated incident beam by means of a dichroic beam splitter so that the ultrasonic wave is generated in the material.

10. The method according to claim 6 further comprising steps of,
    transmitting a high power pulsed laser beam, and
    illuminating the said surface portion of the material with the said high power pulsed laser beam substantially colinearly with the modulated incident beam by means of a dichroic beam splitter so that the ultrasonic wave is generated in the material.

11. An optical apparatus for measuring the Doppler shift produced in a beam of coherent light when the said beam is scattered by a surface portion of a material undergoing deformation responsive to the presence of an ultrasonic wave comprising:
    a laser system for transmitting an incident beam of coherent light,
    modulation means for phase modulating the said incident beam by a predetermined frequency $f_M$,
    optical assembly means for directing the said modulated incident beam toward the surface portion of the material undergoing the deformation to produce a scattered beam therefrom and for transmitting the said scattered beam,
    an interferometer of the confocal Fabry-Perot type exhibiting a frequency response curve having a peak disposed in the path of the scattered beam transmitted by the optical assembly means for producing an optical interferometer signal, photodetecting means for detecting the said optical interferometer signal to generate an electrical signal responsive thereto, output circuit means for processing the said electrical signal to produce an output indicative of the Doppler shift in the scattered beam, calibration circuit means having a bandpass filter tuned at the said predetermined frequency $f_M$ and being connected to the output circuit to produce a calibration signal, and feedback means for feeding back the calibration signal to the output circuit means so that the said output is calibrated in real time.

12. The optical apparatus according to claim 11 wherein, the optical assembly means include focussing means to project the modulated incident beam onto the surface portion and to receive the scattered beam therefrom, polarizing means for polarizing the modulated incident beam and the scattered beam differently from each other, and first polarizing beam splitting means to direct the modulated incident beam toward the surface portion in a direction substantially normal thereto and to direct the scattered beam toward the interferometer.

13. The optical apparatus according to claim 12 wherein the laser system includes tuning means for adjusting the frequency of the coherent light in the incident beam, the optical apparatus further comprising, stabilization circuit means connected to the photodetecting means and including a high frequency lock-in amplifier to which a reference signal of the frequency $2f_M$ is applied, and adapted to detect the second harmonics of the said electrical signal from the photodetecting means and to produce a stabilization signal responsive thereto, and means applying the stabilization signal to the said tuning means to adjust the frequency of the coherent light to match the frequency corresponding to a zero of the second derivative of the said frequency responsive curve of the interferometer.

14. The optical apparatus according to claim 13 wherein the laser system is a multi-mode laser system.

15. The optical apparatus according to claim 12 wherein, the laser system includes tuning means for adjusting the frequency of the coherent light in the incident beam, the said tuning means comprising two tuning mechanisms, one for slow response frequency control and another for fast response frequency control, the optical apparatus further comprising frequency locking means which comprise, amplitude fluctuation detecting means disposed in the path of the incident beam of coherent light for generating an amplitude fluctuation signal, frequency fluctuation detecting means adapted to transmit a portion of the incident beam of coherent light through the said interferometer colinearly with the scattered beam and to detect the incident beam which has passed through the interferometer for generating a frequency fluctuation signal, signal processing means for processing the amplitude fluctuation signal and the frequency fluctuation signal to produce a first signal and a second signal, and means connecting the tuning means and the signal processing means for applying the said first signal to one of the two tuning mechanisms and the second signal to the other to adjust the frequency of the coherent light so that the frequency of the incident beam is set at about half maximum of the peak of the frequency response curve of the interferometer.

16. The optical apparatus according to claim 15 wherein the frequency fluctuation detecting means comprise, a detector producing a frequency fluctuation signal, second polarizing beam splitting means disposed in the path of the scattered beam to transmit the portion of the incident beam through the said interferometer colinearly with the scattered beam, and third polarizing beam splitting means disposed in the path of the said optical interferometer signal to direct the scattered beam toward the photodetecting means and the portion of the incident beam toward the said detector.

17. The optical apparatus according to claim 16 wherein the laser system is a multi-mode laser system.

18. The optical apparatus according to claim 11 further comprising:

a high power laser system for transmitting a pulsed high power laser beam, and means for illuminating the said surface portion with the said high power pulsed laser beam substantially colinearly with the modulated incident beam by means of a dichroic beam splitter so that the ultrasonic wave is generated in the material.

19. The optical apparatus according to claim 13 further comprising:

a high power laser system for transmitting a pulsed high power laser beam, and means for illuminating the said surface portion with the said high power pulsed laser beam substantially colinearly with the modulated incident beam by means of a dichroic beam splitter so that the ultrasonic wave is generated in the material.

20. The optical apparatus according to claim 16 further comprising:

a high power laser system for transmitting a pulsed high power laser beam, and means for illuminating the said surface portion with the said high power pulsed laser beam substantially colinearly with the modulated incident beam by means of a dichroic beam splitter so that the ultrasonic wave is generated in the material.

* * * * *